(12) United States Patent
Bernhardt

(10) Patent No.: US 7,372,943 B2
(45) Date of Patent: May 13, 2008

(54) METHOD FOR RECORDING PROJECTION IMAGE

(75) Inventor: Philipp Bernhardt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/639,159

(22) Filed: Dec. 14, 2006

(65) Prior Publication Data

US 2007/0217573 A1    Sep. 20, 2007

(30) Foreign Application Priority Data

Dec. 21, 2005   (DE) .................. 10 2005 061357

(51) Int. Cl.
*H05G 1/64* (2006.01)
(52) U.S. Cl. .................. 378/98.12; 378/98.9

(58) Field of Classification Search .................. 378/5, 378/98.9, 98.11, 98.12
See application file for complete search history.

(56) References Cited

U.S. PATENT DOCUMENTS

| 5,648,997 A | 7/1997 | Chao .................. 378/98.4 |
| 6,343,111 B1 | 1/2002 | Avinash et al. .......... 378/98.11 |
| 2002/0075997 A1* | 6/2002 | Unger et al. ............. 378/98.9 |

* cited by examiner

*Primary Examiner*—Courtney Thomas

(57) ABSTRACT

In recording projection images for dual absorptiometry, the optical thickness of an object being examined is determined on the basis of a projection image recorded in a high-energy range, and parameters for recording a projection image in the low-energy range are selected as a function of the determined optical thickness. The ratio between image quality and the radiation dosage of the object being examined can be optimized thereby.

18 Claims, 2 Drawing Sheets

METHOD FOR RECORDING PROJECTION IMAGE

CROSS REFERENCE TO RELATED APPLICATIONS

This application claims priority of German application No. 10 2005 061 357.8 filed Dec. 21, 2005, which is incorporated by reference herein in its entirety.

FIELD OF THE INVENTION

The invention relates to a method for recording projection images of an object being examined, the projection images being recorded in different energy ranges and further processed to produce a combined image.

BACKGROUND OF THE INVENTION

A device of said type is known from U.S. Pat. No. 6,343,111 B1. Said known device includes a recording device having an x-ray source and an x-ray detector. Projection images of an object being examined can be recorded successively in a high-energy range and a low-energy range by means of said recording device. A combined image can then be produced by an evaluation unit from the projection images recorded in the high-energy and low-energy range.

Because the absorption behavior of the irradiated material of the object being examined differs depending on the energy of the irradiating beam, by combining the projection images it is possible to produce combined images reproducing the structural distribution of a specific material within the object being examined. For example structural distributions of two different materials having different absorption characteristics can be resolved when two projection images are recorded in different energy ranges.

The quality of the combined images will therein be all the better the further apart the high-energy range and low-energy range are. It is furthermore necessary to set the recording device's recording parameters in such a way that projection images exhibiting a sufficiently good signal-to-noise ratio will be produced in both the high-energy and low-energy range so that the image quality of the combined image will also be good. It must, though, be noted in this regard that in order to avoid motion artifacts the projection images must be recorded within a short interval one after the other in the high-energy and low-energy range. Moreover, the exposure to radiation of the object being examined must as a rule be kept as low as possible. The recording device's recording parameters must for this purpose be matched to the absorption characteristics of the object being examined.

Matching of said type does not, though, take place in the case of the known method.

SUMMARY OF THE INVENTION

Proceeding from this prior art, the object of the invention is therefore to disclose an adaptive method for recording projection images for minimizing the exposure to radiation of the object being examined.

Said object is achieved by means of a method having the features of the independent claim. Advantageous embodiments and developments are indicated in claims dependent thereon.

With said method, the optical thickness in a second energy range of the object being examined is approximately determined by the evaluation unit using a projection image recorded in a first high-energy range. The evaluation unit then sets recording parameters for recording the projection image in the second energy range as a function of the determined optical thickness of the object being examined. It is possible, using the determined optical thickness, to minimize the exposure to radiation of the object being examined and maximize the image quality of the projection image recorded in the second energy range, taking account of the required exposure time and the radiating power the radiation source is capable of producing. Overall, the exposure to radiation of the object being examined can thus be kept low.

In a preferred embodiment the optical thickness in the low-energy range of the object being examined is approximately determined by the evaluation unit using the projection image recorded in the high-energy range. The evaluation unit then sets the recording device's recording parameters, in particular those of the radiation source and detector, as a function of the determined optical thickness of the object being examined. Because the effective cross-section of the radiation quanta in terms of their impact on the material of the object being examined decreases as the quantum energy increases, a projection image recorded in the high-energy range will result in less exposure to radiation of the object being examined since fewer absorption processes take place than in the case of lower energy levels. Moreover, the recording parameters can only be poorly optimized in the case of high energy levels owing to the spectrum's wide distribution. The optical thickness in the low-energy range of the object being examined can, however, be approximately determined using the projection image recorded in the high-energy range. If the optical thickness in the low-energy range is known, recording parameters of the recording device that are matched to the optical thickness of the object being examined can be selected and set. The exposure to radiation tending to be higher during projection recording in the low-energy range can thereby be reduced to the extent necessary in keeping with the absorption characteristics of the object being examined.

In a preferred embodiment the ratio between the signal-to-noise ratio of the projection image recorded in the low-energy range and the exposure to radiation of the object being examined is maximized through the choice of recording parameters in the low-energy range, taking account of the pre-specified exposure time and the radiating power the radiation source is capable of producing. A setting of said type will, taking account of the performance capability of the radiation source, enable the optimal image quality to be achieved with the exposure to radiation of the object being examined being minimized.

The recording parameters selected by the evaluation unit for recording the projection image in the low-energy range are read out by the evaluation unit from a predefined table preferably as a function of the determined optical thickness of the object being examined and required exposure time. The advantage thereof is that the recording parameters will not have to be recalculated every time, thus making the process of determining the recording parameters low in compute intensiveness. It is furthermore possible to incorporate experience-based knowledge into the tables.

In a further preferred embodiment the radiation source is an x-ray source and the detector is an x-ray detector. If the x-ray source is an x-ray tube, then the recording parameters requiring to be set are the tube voltage, the tube current, the material and thickness of any preliminary filters that may be present, and the exposure time. Exposure to radiation in the case of medical applications can be not insubstantially reduced for a patient thanks to adaptive setting of the recording parameters for recording in the low-energy range. The image quality of the combined image can furthermore be increased.

BRIEF DESCRIPTION OF THE DRAWINGS

Further specifics and advantages of the invention will emerge from the following description in which exemplary embodiments of the invention are explained in detail with the aid of the attached drawing.

DETAILED DESCRIPTION OF THE INVENTION

Figure 1:
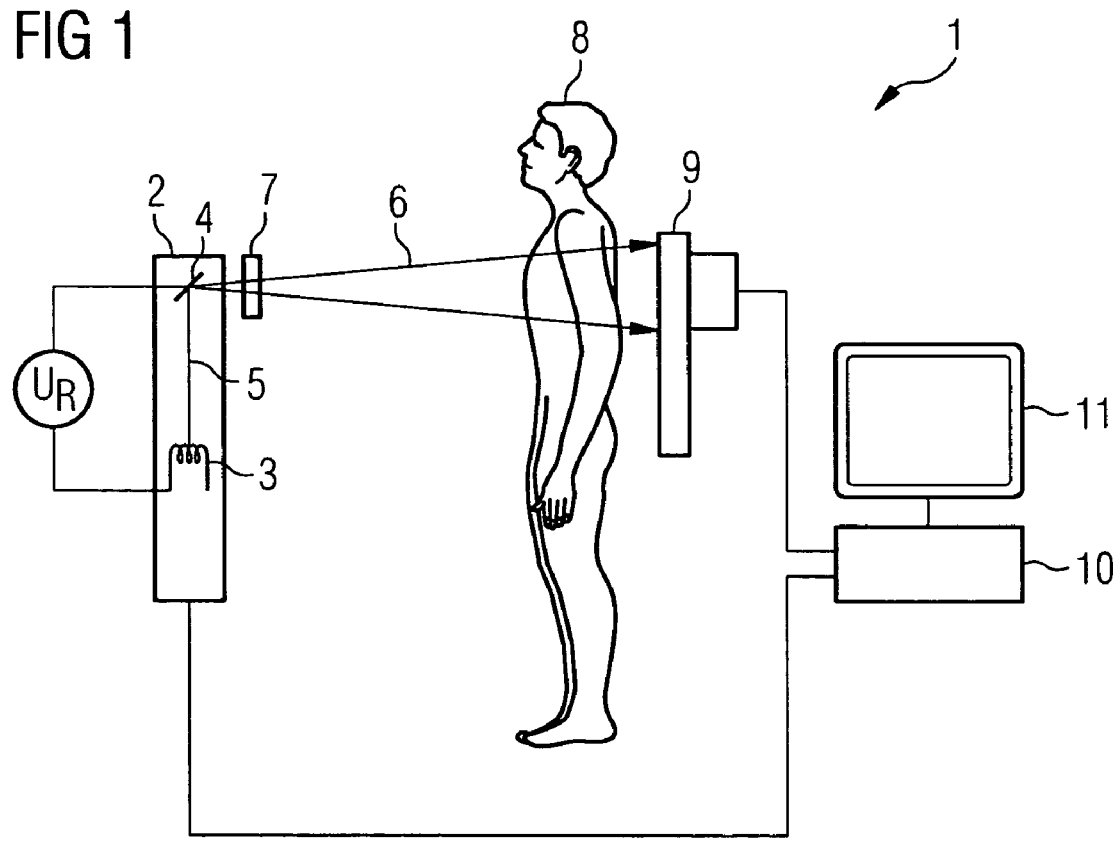
FIG. 1 is a schematic of an x-ray system with which x-ray recordings for dual x-ray absorptiometry can be produced.

FIG. 1 shows an x-ray system 1 with which x-ray recordings for dual x-ray absorptiometry can be produced. The x-ray system 1 includes an x-ray tube 2 having a cathode 3 for emitting electrons. The cathode 3 is as a rule formed from an incandescent filament through which a heater current $I_R$ flows. The electrons emitted by the cathode 3 are accelerated toward an anode 4 with the aid of a tube voltage $U_R$. That produces an electron beam 5 that impinges on the anode 4 in a focused spot. The electrons retarded in the anode 4 produce x-radiation 6 which first passes through a preliminary filter 7 to suppress the low-energy component. The preliminary filters 7 are as a rule copper plates that can be interposed having different thickness into the beam path of the x-radiation 6. The x-radiation 6 then penetrates a patient 8 being examined.

The x-radiation 6 that has passed through the patient 8 impinges on an x-ray detector 9 that produces an absorption image of the patient 8, with the structure of the material in the patient 8 that absorbs x-radiation 6 being projected onto the x-ray detector 9.

Connected downstream of the x-ray detector 9 is an evaluation unit 10 which also applies control signals to the x-ray tube 2. The evaluation unit 10 linearly combines the absorption images recorded through varying the tube voltage $U_R$ in different energy ranges of the x-radiation 6 and, with the aid of a display unit 11, displays the combined image produced by linearly combining the individual absorption images. Linearly combining the absorption images can entail, for example, forming a difference through which the bone structure of the patient 8 is eliminated from the combined image. The combined image produced in this way contains the absorption structure of the soft tissue, which is advantageous particularly in the case of pulmonary examinations.

To ensure the linear independence of the absorption images in the different energy ranges, the spectra of the x-radiation 6 used for recording the respective absorption images should overlap as little as possible. That can be achieved by, for example, varying the tube voltage $U_R$ and the preliminary filters 7. A low tube voltage $U_R$ can, for example, be used for the absorption image in the low-energy range. The preliminary filters 7 can furthermore exhibit a small material thickness so that the low-energy component of the spectrum produced by the x-ray tube 2 will be only moderately suppressed. Conversely, a high tube voltage $U_R$ can be used for the absorption images in the high-energy range. Preliminary filters 7 having a large material thickness can furthermore also be used that allow only the high-energy component of the spectrum produced by the x-ray tube 2 to pass through.

The utilization factor of the x-ray tube 2 rises as a rule linearly with the applied tube voltage $U_R$. Moreover, the effective cross-section of the x-ray quanta in terms of their impact on the material decreases as the quantum energy increases. For these reasons, with the same exposure times and x-ray currents, the x-ray detector 9 will receive a higher detector dosage in the case of an x-ray recording in the high-energy range than in the case of x-ray recordings in the low-energy range because the radiating power generated by the x-ray tube 2 will be greater in the high-energy range than in the low-energy range and because more x-ray quanta will penetrate the patient 8. So in order to obtain an adequate detector dosage in the case of an x-ray recording in the low-energy range the tube current $I_R$ must be high and the exposure time long. Because the tube current $I_R$ can be more readily increased by heating than decreased, the x-ray recording is as a rule first produced using a high tube voltage $U_R$ and short exposure times, then the x-ray recording is produced using a low tube voltage $U_R$ and long exposure times. It must, though, be noted in this regard that the tube current $I_R$ cannot be increased at will, nor can the exposure time be prolonged at will because motion artifacts will otherwise occur in the absorption images. Owing to the higher absorption in the low-energy range, for an adequate detector dosage it is therefore necessary either to raise the tube voltage $U_R$ or to reduce the material thickness of the preliminary filters 7. The recording parameters necessary for producing the x-ray recording in the low-energy range, which is to say the tube voltage $U_R$, the tube current $I_R$, the material properties and thickness of the preliminary filters 7, and the exposure time of the x-ray detector 9, therefore have to be selected as a function of the optical thickness of the patient 8.

Figure 2:
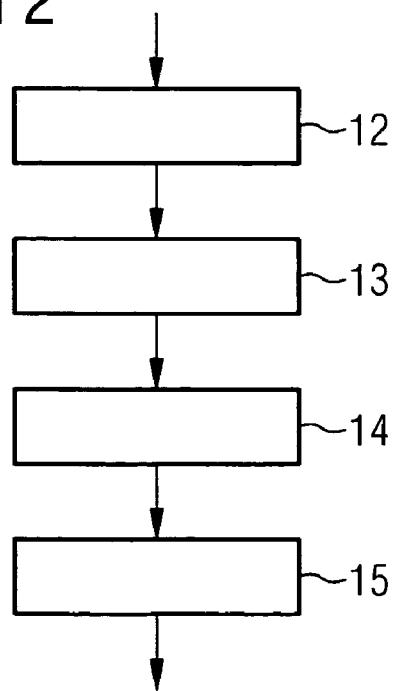
FIG. 2 is a flowchart of a method for performing dual x-ray absorptiometry.

FIG. 2 is a flowchart of a method by means of which the recording parameters of the x-ray tube 2 and x-ray detector 9 can be set automatically.

With the method shown in FIG. 2 a high-energy recording 12 is first produced using default values for the recording parameters. That is because, owing to the wide distribution of the retardation spectrum, the recording parameters for the high-energy recording 12 cannot be easily optimized for the respective optical thickness of the patient 8. Moreover, the patient's dosage $D_P$ is as a rule lower in the case of x-ray recordings in the high-energy range than in the low-energy range.

The high-energy recording 12 is followed by equivalent-value determining 13. An equivalent value of a comparable material can be calculated as part of this procedural step from the data of the high-energy recording 12, which is to say from the tube voltage $U_R$, the tube current $I_R$, the exposure time and the type of preliminary filters 7, and the detector dosage registered by the x-ray detector 9. Said equivalent value describes the mean height a column of the comparable material arranged between the x-ray tube 2 and x-ray detector 9 would need to have to exhibit the same x-ray absorption as the object being examined. Said comparable material should therein be made of atoms having an atomic number close to a mean atomic number of the atoms comprising the object being examined. Water is as a rule used as comparable material for the examination of a patient 8.

The evaluation unit 10 uses the determined equivalent value to make a selection 14 of the recording parameters for a low-energy recording 15. The recording parameters for the low-energy recording 15 are therein selected in such a way that the image quality of the low-energy recording will be as high as possible and the patient's dosage $D_P$ as low as possible. Other conditions that apply to selecting the recording parameters are ensuring an optimal separation of the spectra used for the high-energy recording 12 and low-energy recording 15 as well as adherence to the limiting values for the recording parameters, particularly to the upper limiting value for the tube current $I_R$.

Figure 3:
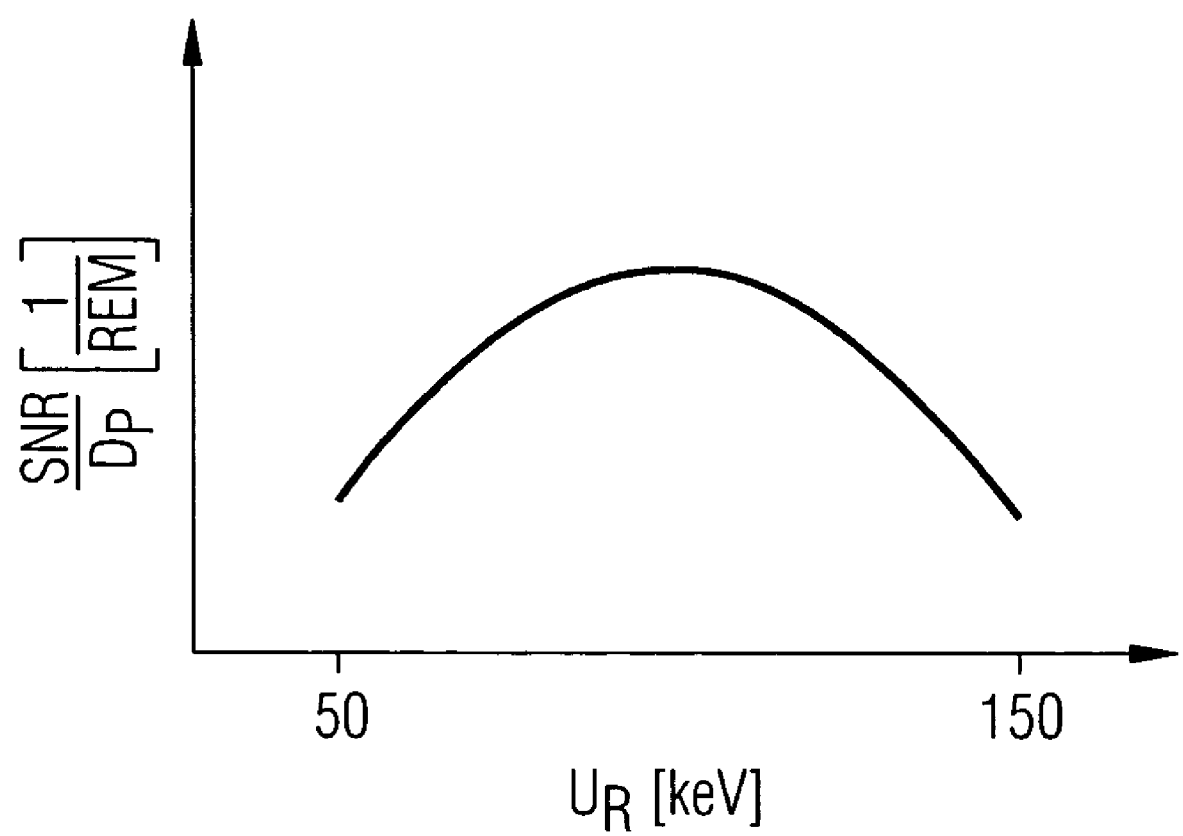
FIG. 3 is a chart on which is plotted a typical curve of the ratio between the signal-to-noise ratio and a patient's dosage as a function of the tube voltage of an x-ray source.

Selecting of the recording parameters is explained in more detail below with the aid of FIG. 3. In FIG. 3 the ratio between the signal-to-noise ratio and the patient's dosage $D_p$ has been plotted for different tube voltages $U_R$.

For recordings of the thorax, the signal-to-noise ratio (=SNR) exhibits a maximum in the 50 to 150 keV energy range because the x-radiation 6 will be almost totally absorbed at low energy levels while at high energy levels for the x-ray quanta said quanta will undergo only slight absorption. The patient's dosage $D_P$ will therefore continually decrease from low to high energy levels with a tube current and exposure time that are constant. The ratio between the signal-to-noise ratio and the patient's dosage $D_P$ will therefore as a rule exhibit a maximum. Provided the spectrum of the x-radiation 6 used for the high-energy recording 12 and the spectrum of the x-radiation 6 used for the low-energy recording 15 are spaced sufficiently apart and the maximum permissible value for the tube current $I_R$ is not exceeded, the values, assigned to said maximum value, for the recording parameters can then be used for the low-energy recording 15.

The respectively suitable settings for the low-energy recording 15 can be pre-tabularized as a function of the equivalent value and read out from a data memory by the evaluation unit 10 when the low-energy recording 15 is being produced.

Optimizing for the low-energy recording 15 can be done automatically. That will prevent recordings having to be repeated owing to an unsuitable recording parameter. The method described here will ensure, moreover, that the respectively most suitable recording parameters are used. The ratio between the combined image's image quality and the patient's dosage $D_P$ will consequently always be optimal.

The method will now be further explained with the aid of a numerical example.

For a pulmonary recording a doctor requires two dual absorption recordings, one produced from the front and one produced from the side. The x-ray system 1 first in each case produces high-energy recordings 12 at a tube voltage $U_R$=120 kV and using a preliminary filter made of copper and having a thickness of 0.3 mm. Using the high-energy recording 12 produced from the front, the evaluation unit 10 calculates an equivalent water value of 200 mm and using the high-energy recording 12 produced from the side it calculates an equivalent water value of 300 mm. The in each case succeeding low-energy recording 15 will therefore be produced using different recording parameters, in the first case at a tube voltage $U_R$=60 kV and using a preliminary filter 7 made of copper and having a thickness of 0.1 mm and in the second case at a tube voltage $U_R$=75 kV and with no preliminary filters 7.

It is noted that the method described here can be used also for other x-ray systems, for example computer-assisted tomography devices, with which x-ray recordings are produced successively in different energy ranges.

It is further noted that the method described here can be used also for other applications, for example for checking luggage or for testing materials.

Attention is finally drawn to the fact that producing the high-energy recording 12 before the low-energy recording 15 offers particular advantages. It is, though, basically also possible to produce the high-energy recording after the low-energy recording and to set the recording parameters for the high-energy recording in keeping with the optical thickness, determined during low-energy recording, of the object being examined. That approach will be expedient whenever exposure to radiation is more serious during high-energy recording than during low-energy recording.

The invention claimed is:

1. A method for generating a combined image of an object from a first and a second projection image irradiated in a first and a second energy range, comprising:
   recording the first projection image in the first energy range using a first recording parameter;
   determining an optical thickness of the object in the second energy range based on the first projection image;
   selecting a second recording parameter in the second energy range as a function of the determined optical thickness of the object;
   recording the second projection image in the second energy range using the determined second recording parameter; and
   generating the combined image of the object from the first and the second projection image.

2. The method as claimed in claim 1, wherein the first recording parameter is a default recording parameter.

3. The method as claimed in claim 1, wherein the first energy range is a high energy range and the second energy range is a low energy range.

4. The method as claimed in claim 1, wherein the optical thickness of the object is a column height of a material having an atomic number comparable to a mean atomic number of the object.

5. The method as claimed in claim 1, wherein the second recording parameter is determined in order to maximize a ratio between a signal-to-noise ratio and a dosage of the object based on a pre-specified exposure time and a possible radiating power.

6. The method as claimed in claim 1, wherein the second recording parameter is selected from a predefined table.

7. The method as claimed in claim 1, wherein the first and the second projection image is recorded by an x-ray image recording device comprising an x-ray tube.

8. The method as claimed in claim 7, wherein the second recording parameter is selected from the group consisting of: a tube voltage of the x-ray tube, a tube current of the x-ray tube, a type of a preliminary filter of the x-ray tube, and an exposure time on the object.

9. The method as claimed in claim 1, wherein the combined image of the object is generated by linearly combing the first and the second projection image.

10. The method as claimed in claim 1, wherein the steps of determining, selecting, and recording are repeated for a plurality of further energy ranges and the combined image is generated by linearly combining the first, the second and a plurality of further projection images respectively recorded in the further energy ranges.

11. The method as claimed in claim 1, wherein the object is a patient.

12. The method as claimed in claim 11, wherein the first and the second projection image is recorded in an area of a thorax of the patient.

13. The method as claimed in claim 1, wherein the object is a luggage.

14. The method as claimed in claim 1, wherein the first energy range is a low energy range and the second energy range is a high energy range.

15. A device for recording a first and a second projection image of an object irradiated in a first and a second energy range, comprising:
    a radiation source that emits radiations on the object in the first and the second energy range;
    a detector that records the first projection image in the first energy range using a first recording parameter and the second projection image in the second energy range using a second recording parameter; and
    an evaluation unit connected with the detector that:
        determines an optical thickness of the object in the second energy range based on the first projection image,
        selects the second recording parameter in the second energy range as a function of the determined optical thickness of the object.

16. The device as claimed in claim 15, wherein the first recording parameter is a default recording parameter.

17. The device as claimed in claim 15, wherein the first energy range is a high energy range and the second energy range is a low energy range.

18. The device as claimed in claim 15, wherein the first energy range is a low energy range and the second energy range is a high energy range.

* * * * *